US010856819B2

(12) United States Patent
Gordon (10) Patent No.: US 10,856,819 B2
(45) Date of Patent: *Dec. 8, 2020

(54) LOCK-BLOCK SHIELD DEVICE

(71) Applicant: Radux Devices, LLC, Omaha, NE (US)

(72) Inventor: Gregory Gordon, Omaha, NE (US)

(73) Assignee: Radux Devices, LLC, Omaha, NE (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/006,036

(22) Filed: Jun. 12, 2018

(65) Prior Publication Data

US 2018/0289343 A1 Oct. 11, 2018

Related U.S. Application Data

(63) Continuation of application No. 15/022,104, filed as application No. PCT/US2014/056585 on Sep. 19, 2014, now Pat. No. 10,010,297.

(Continued)

(51) Int. Cl.
*A61B 6/10* (2006.01)
*G21F 3/00* (2006.01)
(Continued)

(52) U.S. Cl.
CPC .............. *A61B 6/107* (2013.01); *A61B 90/05* (2016.02); *G21F 3/00* (2013.01); *A61B 90/50* (2016.02); *A61B 2090/0481* (2016.02)

(58) Field of Classification Search
CPC . A61B 2090/0481; A61B 6/107; A61B 90/05; A61B 90/50; G21F 3/00
See application file for complete search history.

(56) References Cited

U.S. PATENT DOCUMENTS 1,772,478 A  8/1930  Came
2,497,749 A  2/1950  Wagner
(Continued)

FOREIGN PATENT DOCUMENTS

CA  2091608  9/1994
DE  2714859  10/1978
(Continued)

OTHER PUBLICATIONS

Gershov, I.Y. Properties and uses of barium ferrite ceramic magnets. Powder Metall Met Ceram 2, 227-234 (1963). https://doi.org/10.1007/BF00774277 (Year: 1963).*

(Continued)

*Primary Examiner* — Wyatt A Stoffa
(74) *Attorney, Agent, or Firm* — Fish & Richardson P.C.

(57) ABSTRACT

Apparatus and techniques for blocking radiation in a medical environment are described. In one or more embodiments, a lock-block shield device includes a base that is configured to adhesively couple to an object associated with a patient. In some embodiments, the base includes a lock mechanism for securing a work piece that has a generally tubular shape. A shield that is configured to at least partially block transmission of radiation can be coupled to the base in a releasable manner. For example, a clasp is used to secure the base and shield together. In embodiments, a ball and socket joint couples the shield and base to permit, for example, the shield to pivot and articulate with respect to the base.

15 Claims, 5 Drawing Sheets

Related U.S. Application Data (60) Provisional application No. 61/880,216, filed on Sep. 20, 2013.

(51) Int. Cl.
*A61B 90/00* (2016.01)
*A61B 90/50* (2016.01)

(56) References Cited

U.S. PATENT DOCUMENTS

| | | | |
|---|---|---|---|
| 2,794,128 A * | 5/1957 | Shasky | G21F 3/02 |
| | | | 250/519.1 |
| 3,016,255 A | 1/1962 | Russel | |
| 3,172,240 A | 3/1965 | Giardini et al. | |
| 3,239,669 A | 3/1966 | Weinberger | |
| 3,303,717 A | 2/1967 | Valenti | |
| 3,409,317 A * | 11/1968 | Richards | F16C 11/106 |
| | | | 403/138 |
| 3,883,749 A | 5/1975 | Whittaker et al. | |
| 4,220,867 A | 9/1980 | Bloch, Jr. | |
| 4,280,056 A | 7/1981 | Renshaw | |
| 4,581,538 A * | 4/1986 | Lenhart | G21F 3/00 |
| | | | 250/515.1 |
| 4,751,747 A | 6/1988 | Banks et al. | |
| D300,945 S * | 5/1989 | Fleming | D24/158 |
| 4,872,714 A | 10/1989 | Brusasco | |
| 4,917,413 A | 4/1990 | Jason et al. | |
| 4,923,162 A * | 5/1990 | Fleming | A61B 6/107 |
| | | | 248/276.1 |
| 4,938,233 A | 7/1990 | Orrison, Jr. | |
| 5,016,292 A | 5/1991 | Rademacher | |
| 5,090,044 A * | 2/1992 | Kobayashi | A61B 6/107 |
| | | | 250/515.1 |
| 5,125,115 A | 6/1992 | Lincoln | |
| RE34,120 E * | 11/1992 | Plahn | B60R 11/02 |
| | | | 248/206.3 |
| 5,319,349 A | 6/1994 | Smith | |
| D349,577 S * | 8/1994 | Sayles | D24/232 |
| 5,398,176 A * | 3/1995 | Ahuja | F16M 11/14 |
| | | | 248/160 |
| 5,417,225 A * | 5/1995 | Rubenstein | A61B 90/04 |
| | | | 128/849 |
| 5,521,803 A | 5/1996 | Eckert | |
| 5,522,403 A * | 6/1996 | Bark | A61B 46/00 |
| | | | 128/849 |
| 5,523,581 A | 6/1996 | Cadwalader | |
| 5,569,090 A | 10/1996 | Hoskins et al. | |
| 5,628,062 A | 5/1997 | Tseng | |
| 5,638,545 A | 6/1997 | Rosner | |
| 5,704,662 A | 1/1998 | Kwiatkowski | |
| 5,711,027 A | 1/1998 | Katz et al. | |
| 5,949,020 A | 9/1999 | Mitchell et al. | |
| 5,981,964 A * | 11/1999 | McAuley | G21F 3/00 |
| | | | 250/515.1 |
| 5,992,823 A | 11/1999 | Hung-Lin et al. | |
| 6,135,032 A | 10/2000 | Ko et al. | |
| 6,217,087 B1 | 4/2001 | Fuller et al. | |
| 6,325,538 B1 * | 12/2001 | Heesch | A61B 6/107 |
| | | | 128/846 |
| 6,394,724 B1 | 5/2002 | Kelly et al. | |
| 6,703,632 B1 * | 3/2004 | Macklis | A61N 5/10 |
| | | | 250/515.1 |
| 7,099,427 B2 * | 8/2006 | Cadwalader | A61B 6/4423 |
| | | | 378/4 |
| 7,112,811 B2 * | 9/2006 | Lemer | G21F 3/00 |
| | | | 250/515.1 |
| 7,188,625 B2 * | 3/2007 | Durette | A61F 9/04 |
| | | | 128/858 |
| 7,226,234 B2 | 6/2007 | Gordy et al. | |
| 7,521,615 B1 | 4/2009 | Ho et al. | |
| 7,663,128 B2 * | 2/2010 | Arterson | A61B 6/4423 |
| | | | 250/519.1 |
| 8,015,714 B2 | 9/2011 | Dekort et al. | |
| 8,032,994 B2 | 10/2011 | Waddell et al. | |
| 8,298,245 B2 | 10/2012 | Li | |
| 8,334,524 B2 | 12/2012 | DeMeo et al. | |
| 8,416,513 B1 | 4/2013 | McPherson | |
| 8,445,093 B2 * | 5/2013 | Lemer | A61B 6/107 |
| | | | 428/131 |
| 8,664,628 B2 * | 3/2014 | Yoder | G21F 3/00 |
| | | | 250/515.1 |
| 8,674,330 B2 * | 3/2014 | Beck | F16M 11/42 |
| | | | 250/516.1 |
| 8,835,887 B2 * | 9/2014 | Beck | A61B 6/4423 |
| | | | 250/515.1 |
| D716,449 S * | 10/2014 | Ballsieper | D24/158 |
| 8,933,426 B2 * | 1/2015 | Rees | A61B 6/4423 |
| | | | 250/516.1 |
| D772,415 S * | 11/2016 | Ballsieper | D24/158 |
| D775,340 S * | 12/2016 | Ballsieper | D24/158 |
| 9,697,920 B2 | 7/2017 | Gordon et al. | |
| 9,728,290 B2 * | 8/2017 | Weed | G01V 5/0016 |
| 10,010,297 B2 | 7/2018 | Gordon | |
| 2002/0174872 A1 | 11/2002 | Cyphers | |
| 2003/0132639 A1 | 7/2003 | Franklin | |
| 2003/0209387 A1 | 11/2003 | Burr | |
| 2004/0041107 A1 * | 3/2004 | Cadwalader | G21F 1/106 |
| | | | 250/519.1 |
| 2004/0169114 A1 | 9/2004 | Dierkes | |
| 2004/0183316 A1 | 9/2004 | Walls et al. | |
| 2005/0023842 A1 | 2/2005 | Johnson et al. | |
| 2005/0104435 A1 | 5/2005 | Bain et al. | |
| 2006/0089626 A1 | 4/2006 | Vlegele | |
| 2007/0029513 A1 * | 2/2007 | Treuth | A61B 6/107 |
| | | | 250/519.1 |
| 2007/0120034 A1 * | 5/2007 | Sparling | A47B 23/046 |
| | | | 248/458 |
| 2007/0297572 A1 | 12/2007 | Moritake et al. | |
| 2008/0056813 A1 | 3/2008 | Viernekes | |
| 2008/0128297 A1 | 6/2008 | Rose | |
| 2008/0164425 A1 * | 7/2008 | Cadwalader | A61B 6/4423 |
| | | | 250/492.1 |
| 2008/0182093 A1 | 7/2008 | Sonntag et al. | |
| 2009/0045358 A1 * | 2/2009 | Arterson | A61B 6/107 |
| | | | 250/519.1 |
| 2009/0232282 A1 | 9/2009 | Belson et al. | |
| 2010/0107320 A1 * | 5/2010 | Rees | A61B 6/4423 |
| | | | 2/456 |
| 2010/0176318 A1 * | 7/2010 | Smith | G21F 1/125 |
| | | | 250/519.1 |
| 2010/0249709 A1 * | 9/2010 | Fischvogt | A61B 17/3421 |
| | | | 604/167.01 |
| 2010/0289718 A1 | 11/2010 | Kang et al. | |
| 2010/0304060 A1 * | 12/2010 | Lemer | A61B 6/4423 |
| | | | 428/34.1 |
| 2011/0248193 A1 * | 10/2011 | Goldstein | A61B 46/00 |
| | | | 250/519.1 |
| 2011/0288489 A1 * | 11/2011 | Bierman | A61M 25/02 |
| | | | 604/180 |
| 2012/0051502 A1 * | 3/2012 | Ohta | A61B 6/022 |
| | | | 378/37 |
| 2012/0086530 A1 * | 4/2012 | Rathbun | H01F 7/0252 |
| | | | 335/285 |
| 2012/0132217 A1 * | 5/2012 | Rees | G21F 3/00 |
| | | | 128/849 |
| 2012/0241652 A1 | 9/2012 | Jeschke | |
| 2012/0246790 A1 | 10/2012 | Salcedo | |
| 2012/0272483 A1 | 11/2012 | Moore | |
| 2012/0324614 A1 | 12/2012 | Steinberg et al. | |
| 2013/0144104 A1 | 6/2013 | Adler | |
| 2013/0254976 A1 * | 10/2013 | Aravena | F42B 39/02 |
| | | | 2/300 |
| 2013/0266122 A1 * | 10/2013 | Patil | A61B 6/107 |
| | | | 378/98 |
| 2013/0320246 A1 | 12/2013 | Beck | |
| 2014/0021377 A1 * | 1/2014 | Khandkar | G21F 1/12 |
| | | | 250/515.1 |
| 2014/0029720 A1 | 1/2014 | Osherov et al. | |
| 2014/0103230 A1 | 4/2014 | Kang | |

(56) References Cited

U.S. PATENT DOCUMENTS

| | | | | |
|---|---|---|---|---|
| 2014/0312083 | A1* | 10/2014 | Scott | A45F 5/021 224/183 |
| 2015/0041686 | A1* | 2/2015 | Pizarro | G21F 3/00 250/519.1 |
| 2015/0195392 | A1 | 7/2015 | Nissenbaum | |
| 2017/0309357 | A1 | 10/2017 | Gordon et al. | |

FOREIGN PATENT DOCUMENTS

| | | |
|---|---|---|
| DE | 3326880 | 2/1985 |
| DE | 202008002237 | 7/2009 |
| EP | 1526603 | 4/2005 |
| EP | 1541897 | 6/2005 |
| FR | 2439460 | 5/1980 |
| GB | 2472246 | 2/2011 |
| JP | S39-009443 | 4/1964 |
| JP | S49-022960 Y | 6/1974 |
| JP | S51-019380 | 2/1976 |
| JP | S52-112075 | 9/1977 |
| JP | H0230096 U | 2/1990 |
| JP | H02-501769 | 6/1990 |
| JP | H03-502182 | 5/1991 |
| JP | H05-038685 | 2/1993 |
| JP | 2003-533245 | 11/2003 |
| JP | 2004-264207 | 9/2004 |
| JP | WO 2004/011824 | 11/2005 |
| JP | 2007-212304 | 8/2007 |
| JP | 2010-521992 | 7/2010 |
| JP | 2010-525910 | 7/2010 |
| JP | 2012135619 | 7/2012 |
| JP | 2013-015369 | 1/2013 |
| JP | 2013-512745 | 4/2013 |
| JP | 2016533246 | 10/2016 |
| KR | 10-2009030459 | 3/2009 |
| WO | WO 1989000831 | 2/1989 |
| WO | WO 1989/05216 | 6/1989 |
| WO | WO 2005/094272 | 10/2005 |
| WO | WO 2006088104 | 8/2006 |
| WO | WO 2008/140486 | 11/2008 |
| WO | WO 2012/049469 | 4/2012 |
| WO | WO 2015/042419 | 3/2015 |

OTHER PUBLICATIONS https://en.wikipedia.org/wiki/Magnetic_field, retrieved Apr. 21, 2020 (Year: 2020).*
https://en.wikipedia.org/wiki/Alpha_particle, retrieved Apr. 21, 2020 (Year: 2020).*
https://en.wikipedia.org/wiki/Polycarbonate, retrieved Apr. 21, 2020 (Year: 2020).*
Extended European Search Report for European Application No. 14/845,264.2, dated Sep. 1, 2016, 11 pages.
Health Physics Society, "Lead Garments (Aprons, Gloves, etc.)," hps.org [online], Aug. 13, 2014 [retrieved on Jan. 12, 2015]. Retrieved from the Internet: <URL:http://hps.org/publicinformation/ate/faqs/leadgarmentsfaq.html>, 8 pages.
International Preliminary Report on Patentability in International Application No. PCT/US2014/056585, dated Mar. 22, 2016, 5 pages.
International Search Report and Written Opinion in International Application No. PCT/US2014/056585, dated Dec. 26, 2014, 8 pages.
Japanese Office Action in Application No. JP2016-544024, dated Jun. 18, 2018, 9 pages (with Machine translation).
Mettler et al., "Radiologic and Nuclear Medicine Studies in the United States and Worldwide: Frequency, Radiation Dose, and Comparison with Other Radiation Sources—1950-2007," Radiology, Nov. 2009, 253(2): 520-531.
Naidu et al., "Radiation exposure to personnel performing endoscopic retrograde cholangiopancreatography," Postgrad Med J., 81(960):660-662, Oct. 2005.
Whitby and Martin, "Investigation using an advanced extremity gamma instrumentation system of options for shielding the hand during the preparation and injection of radiopharmaceuticals," J Radiol Prot., 23(1):79-96, Mar. 2003.
EP Communication pursuant to Article 94(3) EPC in Appln. No. 14845264.2 dated Dec. 4, 2018, 5 pages.
EPO Summons in Application No. 14845264.2, dated Sep. 22, 2020, 9 pages.

\* cited by examiner

LOCK-BLOCK SHIELD DEVICE

CROSS-REFERENCE TO RELATED APPLICATIONS

This application is a continuation of U.S. application Ser. No. 15/022,104, filed Mar. 15, 2016 (now U.S. Pat. No. 10,010,297), which application is a National Stage application under 35 U.S.C. § 371 of International Application No. PCT/US2014/056585, filed Sep. 19, 2014, which claims the benefit of U.S. Provisional Application Ser. No. 61/880,216 filed Sep. 20, 2013. The disclosures of the prior applications are considered part of (and are incorporated by reference in) the disclosure of this application.

BACKGROUND

Radiation protection in the medical field is very important. Procedures and therapies are designed to minimize patient radiation exposure while ensuring physicians and healthcare workers can effectively treat the patient. Attention is being paid, for example, to developing imaging machines that decrease patient radiation exposure by implementing lower radiation levels. Unfortunately, attention is often lagging for protecting healthcare workers such as physicians, nurses, technicians, and so forth from radiation exposure.

Healthcare workers can be exposed to radiation during patient procedures. For example, a physician's hands can be exposed to radiation from imaging machines while inserting a central line in a patient. Healthcare workers' cumulative radiation exposure can be significant as they can perform multiple procedures in a normal day. In the U.S. alone, estimates are that 293 million diagnostic and fluoroscopic procedures are performed annually. *Radiology*, 253:2—November 2009.

Physical barriers can limit radiation exposure. Radiation shielding and body wear are two types of physical barriers used to minimize radiation exposure. These physical barriers have drawbacks. Physical barriers typically are bulky and obtrusive. Physical barriers often times increase orthopedic stress on the person using the body wear and/or inhibit ergonomic efficiency. Lead aprons, one type of body wear, are heavy and place stress on the person's shoulders and neck. Some physicians and fluoroscopic room staff forego physical barriers to avoid one, or more, of these drawbacks. As a result, these personnel may be exposed to higher radiation levels in comparison to instances in which physical barriers are implemented.

SUMMARY

Apparatus and techniques for blocking radiation in a medical environment are described. In one or more embodiments, a lock-block shield device includes a base that is configured to adhesively couple the device to an object associated with a patient. In some embodiments, the base includes a lock mechanism for securing a work piece, which may have a generally tubular shape. A shield configured to at least partially block electromagnetic radiation within a spectrum of wavelengths (e.g., x-ray radiation) can be coupled to the base. For example, a clasp can be used to secure the base and shield together. In embodiments, a stem with a malleable end is configured to be inserted into hole formed in the base to secure the base and shield together. In additional embodiments, a ball and socket joint couples the shield and base to permit, for example, the shield to pivot and articulate with respect to the base.

This Summary is provided solely to introduce subject matter that is fully described in the Detailed Description and Drawings. Accordingly, the Summary should not be considered to describe essential features nor be used to determine scope of the claims.

BRIEF DESCRIPTION OF THE DRAWINGS

The detailed description is described with reference to the accompanying figures. In the figures, the left-most digit(s) of a reference number identifies the figure in which the reference number first appears. The use of the same reference numbers in different instances in the description and the figures may indicate similar or identical items.

3B is exploded view of a lock-block shield device with a clasp-type connection that couples a shield and base in accordance with implementations of the present disclosure.

DETAILED DESCRIPTION

Overview

Physicians and medical personnel sometimes tradeoff radiation protection for ergonomic and procedural efficiency during interventional procedures. Physical barriers used to block radiation typically are heavy due to the presence of lead. Some physicians, for example, do not use or sparingly use physical barriers for radiation protection when inserting catheters or drains because these barriers interfere with workflow or cause orthopedic stress when performing the procedure. As a result, the physician may be exposed to a higher cumulative level of radiation than is recommended on a monthly basis.

Another drawback of physical barriers is that reusable physical barriers can act as a conduit for spreading pathogens between people including patients and medical personnel. A contaminated physical barrier can transmit pathogens such as multi-drug resistant skin pathogen (MRSA) between people. It may be inefficient to clean physical barriers between uses.

Accordingly, a lock-block shield device is configured to at least partially (e.g., partially, substantially, or completely) block potentially harmful radiation (e.g., radiation within a spectrum of wavelengths, such as x-ray radiation, that may be harmful to the human body when the human body is undesirably exposed to the radiation source) is described. In embodiments, the lock-block shield device is disposable or suitable for single use to avoid transmitting pathogens between patients.

In embodiments, the lock-block shield device includes a base and a shield for blocking radiation in medical situations. The base and shield are connected to one another by a clasp mechanism. The base is constructed to adhesively secure the device to an object, such as a patient or an object associated with the patient, and the shield can be positioned to block radiation. Thus, the lock-block shield device can be arranged to promote ergonomic activity and permit efficient work flow.

The shield and base, in embodiments, are coupled by a ball and socket joint to permit rotation of the shield with respect to the base. In examples, the shield is configured to articulate along an axis that is generally perpendicular to an axis through which the shield can be rotated. In additional examples, the shield and base are coupled by a fixating slot. Accordingly, the shield can be oriented and articulated to readily achieve a desired configuration that blocks radiation for a healthcare worker while minimizing procedural interference.

In embodiments, a lock-block shield device includes a lock mechanism, such as a clamp, for securing a work piece that is generally tubular, such as a catheter, drain, or other tube-like structure, to the base. In embodiments, the lock mechanism can be secured or released with and/or without removal of the shield. Thus, a user such as a physician or other health care worker can position or reposition a catheter while the shield is in place to block radiation directed to the physician.

Example Lock-Block Shield Devices

Figure 1:
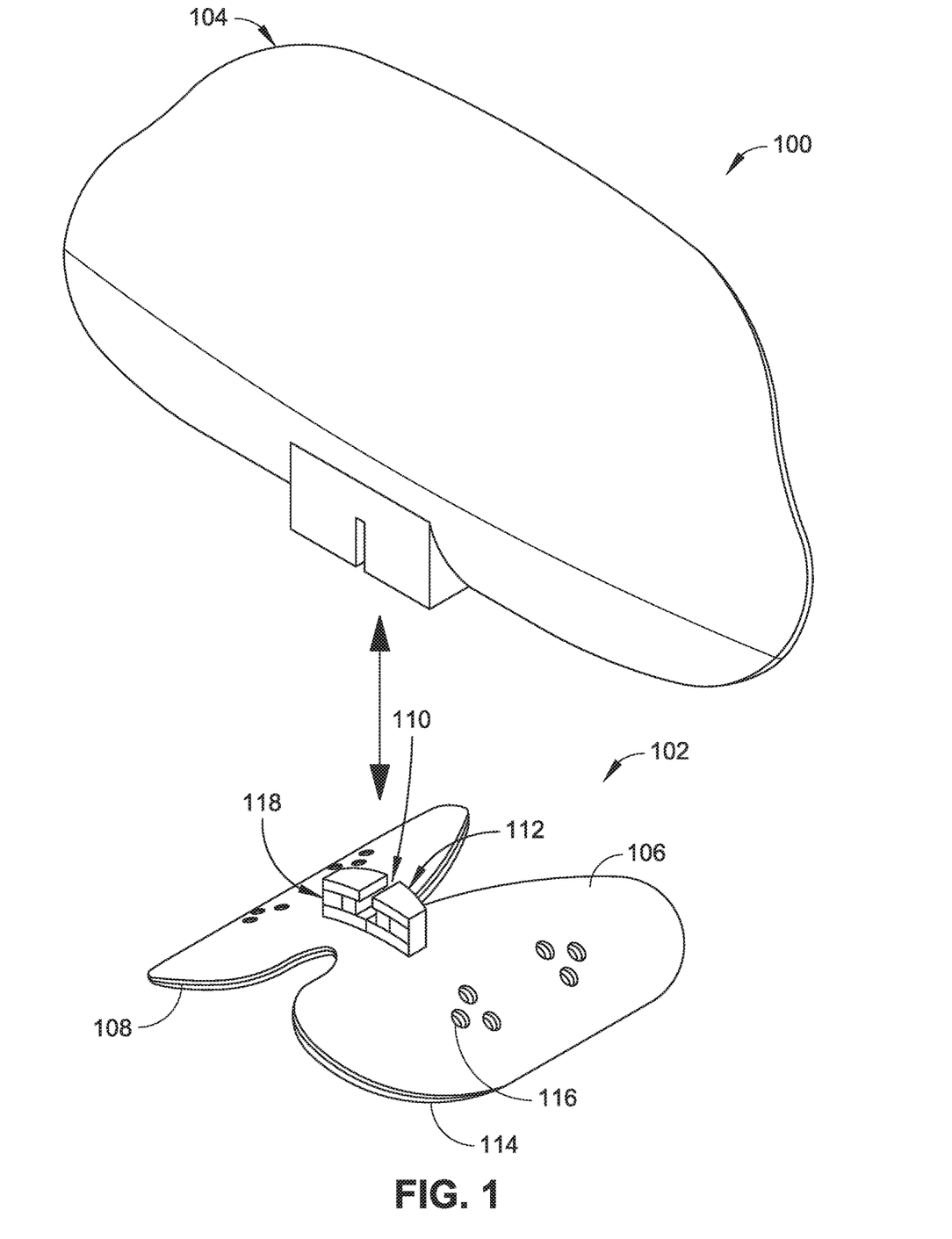
FIG. 1 is an exploded view of a lock-block shield device in accordance with embodiments of the present disclosure.

FIG. 1 illustrates an example lock-block shield device 100. The lock-block shield device 100 includes a base 102 and a shield 104. The base and shield, for example, can be provided as a single use kit that is assembled at a point of use and subsequently disposed of after a procedure to avoid cross-contamination. The shield and/or base can be provided in a variety of sizes, such as small, medium, or large with respect to one another.

The lock-block shield device 100 can be positioned on a patient, for instance, so that it is adjacent to the patient's liver when inserting a bile drain using real-time x-ray imaging. In this manner, the device 100 can shield (e.g., protect) the healthcare worker's hands from the x-ray radiation while allowing the healthcare worker to position his/her hands in an ergonomically effective manner that does not disrupt the worker's workflow. Protecting portions of a healthcare worker's body adjacent to a source of radiation or an area being imaged with x-rays can be beneficial as radiation exposure decreases based on the square of the distance between the radiated area and the object, e.g., a physician's hands. A physician's hands can be exposed to nine times the radiation to which his/her torso is exposed while using real-time x-ray imaging. In examples, the radiation energy is in the rage of and/or approximately 100 KeV.

The base 102 as shown includes a flap 106 that is butterfly shaped and is formed of a plastic suitable for medical applications. Although a flap with a butterfly shape is illustrated, the flap's shape can be varied based on design preference. As illustrated, the flap 106 has a substantially flat surface 108 that allows it to rest on an object. The object can be a patient or an object associated with a patient, e.g., a table, a drape, or the like. In embodiments, the flap 106 is curved or is malleable. For example, the flap 106 is malleable to curve or bend to conform to a patient's torso.

The base 102 can be fabricated from a variety of materials. In embodiments, the base 102 is manufactured from a plastic. In further embodiments, the base and/or flap is formed from a wire or wire-type structure. For example, a metallic wire, coated with a medical grade plastic, may be shaped to form the flap, e.g., formed with a butterfly shape to function as a substantially flat surface on which the lock-block can rest. In implementations, the wire forming the base is malleable to conform to a curved surface. A variety of factors can be considered when selecting a plastic for the base 102. Factors include, but are not limited to, resistance to microbe/bacterial contamination, rigidity, thermal stability, likelihood for triggering an allergic reaction, the plastic's ability to be infused with a radiation blocking material (e.g., accept powdered barium) and the like.

As shown, the base 102 includes a protrusion 110 that extends generally away from the substantially flat surface 108. The protrusion 110 can be used to support the shield 104, to function as a stat lock, or for another purpose or combination of purposes. For example, the protrusion defines a slot 112 that is configured to receive a tube shaped work piece, e.g., a catheter, in order to secure it to the lock-block shield device 100.

In embodiments, the base 102 and/or flap 106 may have a profile that is ramped so that a portion of the base that is to hold the work piece, e.g., a drain, is spaced away from an object on which the base is placed. For example, the base may ramp from 3-5 millimeters to 6-10 millimeters. In embodiments, the protrusion is ramped. For example, the base 102 is substantially flat while the protrusion is ramped. Spacing the work piece away from the object can promote greater freedom of motion to adjust the work piece. The additional freedom may be attributed to the work piece being able to move in x-y directions with respect to the base. Thus, a healthcare worker may more easily adjust a hemostasis valve (an example work piece) by adjusting it in multiple directions.

A foam base 114 is attached to the flat surface 108 of the base illustrated in FIG. 1. The foam base 114 can be made of a suitable medical grade material. The foam base is coated with an adhesive material, e.g., a medical grade adhesive, on a side opposite the flap 106. The lock-block shield device 100 can be provided with a plastic or foil sheet that covers the adhesive and is removed to expose the layer of adhesive material for use.

In embodiments, the foam base 114 is formed of a dense foam with a thickness of in the range of 1 millimeter to 2.5 centimeters. In embodiments, the foam has a thickness of approximately 1 millimeter. The foam can be selected to minimize fluids from absorbing in the foam's voids, user comfort, flexibility, suitability as a substrate for the adhesive, a combination of factors, and so forth.

The adhesive can be selected from a variety of medical grade adhesives based on a variety of factors. For example, the adhesive is selected for its ability to adhere to a patient's skin or to a drape, while still permitting it to release with alcohol (e.g., ethyl alcohol). The adhesive may be chosen to resist water, blood, or other bodily fluids, minimize the likelihood of an allergic reaction by a patient, and so forth.

As shown, the base 102 has one or more apertures 116 that extend through the flap 106 and/or the foam base 112. The apertures 116 are configured for use in suturing the base 102 to an object. A medical worker such as a physician, for instance, can suture the base 102 to a patient's skin through one or more of the apertures in addition to adhere the base to the patient's skin, such as for a patient with an allergy to an adhesive. Other suitable mechanism for securing the base 102 include, but are not limited to, a suction device, one or more straps (e.g., adjustable straps).

As shown in FIG. 1, the base 102 includes a lock mechanism 118 for holding a work piece that has a substantially tubular shape. The lock mechanism 118 can be used to secure a catheter, a drain, an intravenous line, or the like. For example, the lock-block shield device 100 is adhered adjacent to where a catheter exits a patient and the lock mechanism 118 holds the catheter to prevent it from coming loose from the patient. In embodiments, the lock mechanism is configured to secure catheter's in the range of between 4 French to 12 French. The lock mechanism can be configured for a particular size or may be configured for a range of sizes.

The lock mechanism 118 is at least partially housed in the protrusion 110. For example, the lock mechanism is positioned adjacent to a slot in the protrusion to hold a drain that is positioned lengthwise in the slot. The lock mechanism 118, in some embodiments, can accommodate side arms that are included on some work pieces. For example, the lock mechanism can hold a hemostasis valve with side arms that extend from the valve's main body. In this example, the lock mechanism 118 and/or the slot is formed with a channel or recess into which the side arms are received. Having described features of the base generally, an embodiment of a lock mechanism is now described.

Figure 2:
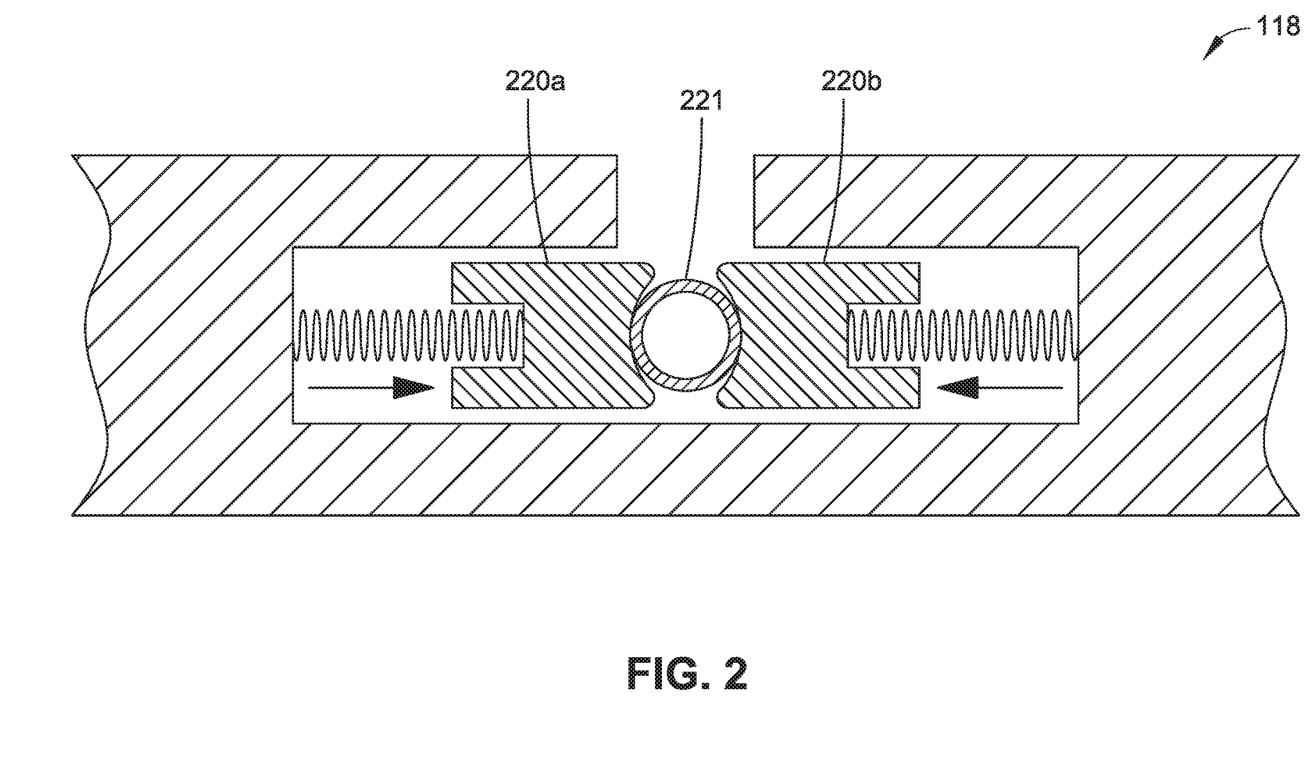
FIG. 2 is a cut-away view of a lock mechanism in accordance with embodiments of the present disclosure.

Referring now to FIG. 2, an embodiment of lock mechanism 118 and its operation are further illustrated and described. As shown, the lock mechanism 118 includes one or more clamps (two are shown, respectively, 220a and 220b) for securing a work piece 221 to the base 102. Although clamp 220a is discussed, it is to be appreciated that additional clamps can be constructed and function in substantially the same manner. In embodiments, the clamp 220a is shaped as a bar that extends along a side of a slot in the protrusion. In the illustrated embodiment, the clamp is biased to engage the work piece 221. In embodiments, the clasp 118 functions to secure or further secure the work piece 221, e.g., the clamps hold the work piece and the clamp pivots to secure the work piece in place like a hinged door. For example, the clamp 220a is biased perpendicular to a tube's primary axis to capture or release the tube as if the tube was held in the stocks. In some embodiments, foam that is sufficiently dense to retain the work piece may be used, e.g., have a spring-type quality. The clamps 220a, 220b may be biased to engage the work piece 221 when not actuated, e.g., the clamp 220a is manipulated to release the work piece 221. In embodiments, a front face of the clamp toward the work piece includes a surface texture or is slightly curved (e.g., a concave surface) to assist in holding the tube. Other lock mechanisms can be used as well. Examples of other lock mechanisms include, but are not limited to, a pivot lock or cam lock.

In embodiments, the lock mechanism 118 is configured to secure and/or release without removal of the shield 104. For example, the clamp 220a is pressed to release or disengage a catheter without dissembling the shield 104 from the base 102. This configuration permits a healthcare worker to adjust the catheter while keeping the shield 104 in place to block radiation.

In implementations, a plug that blocks radiation is included with the lock-block shield device 100. The plug is configured to fit in the lock mechanism 118 and block radiation when no work piece is present. The plug may be used, for example, when the lock-block shield device 100 is used as a radiation shield for a barium swallow. In this example, the plug is inserted in the lock mechanism 118 to prevent radiation from passing through the slot.

Figure 3:
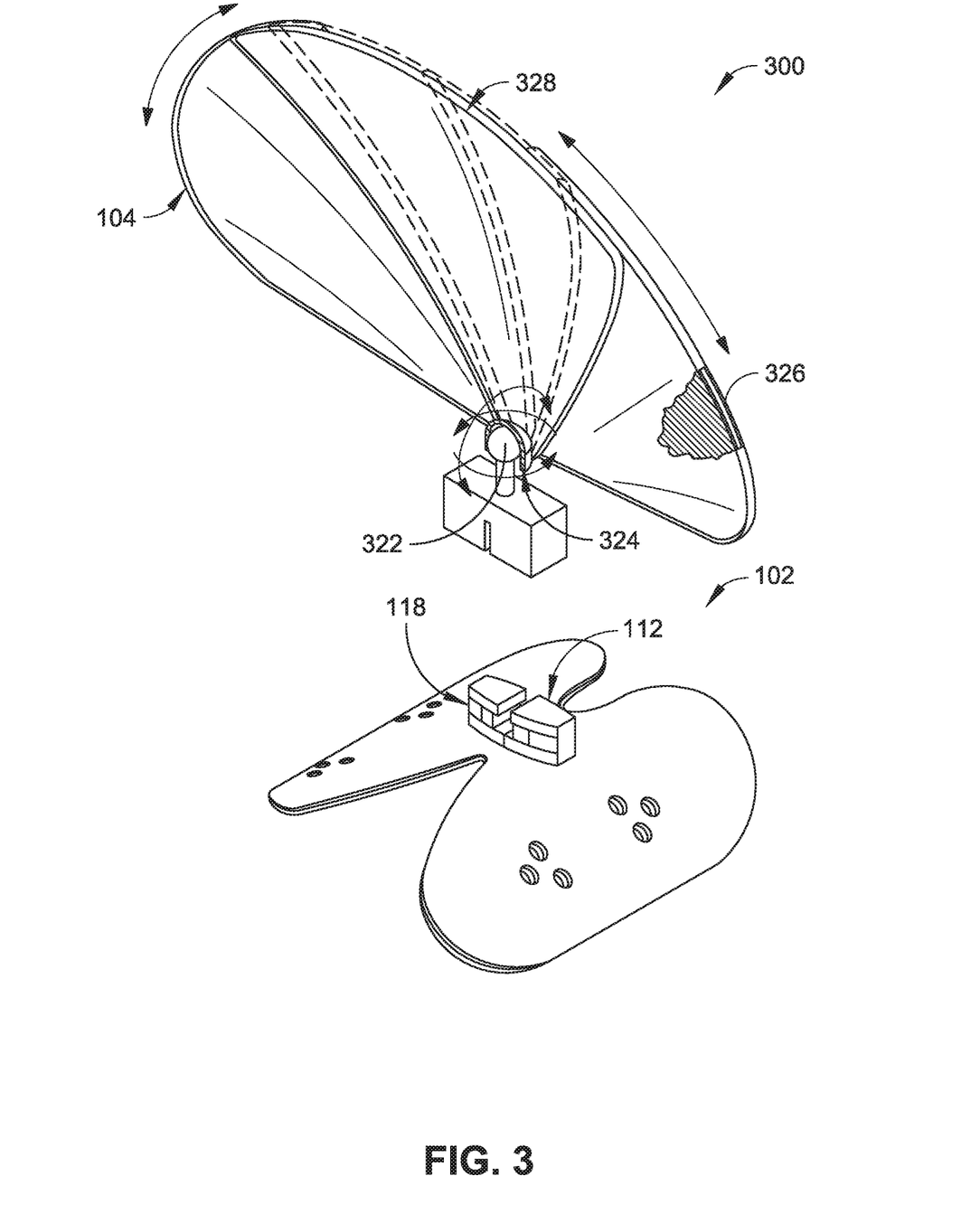
FIG. 3 is a partial cut-away view of a lock-block shield device with a ball- and socket joint that couples a shield and base in accordance with implementations of the present disclosure.
Figure 3A:
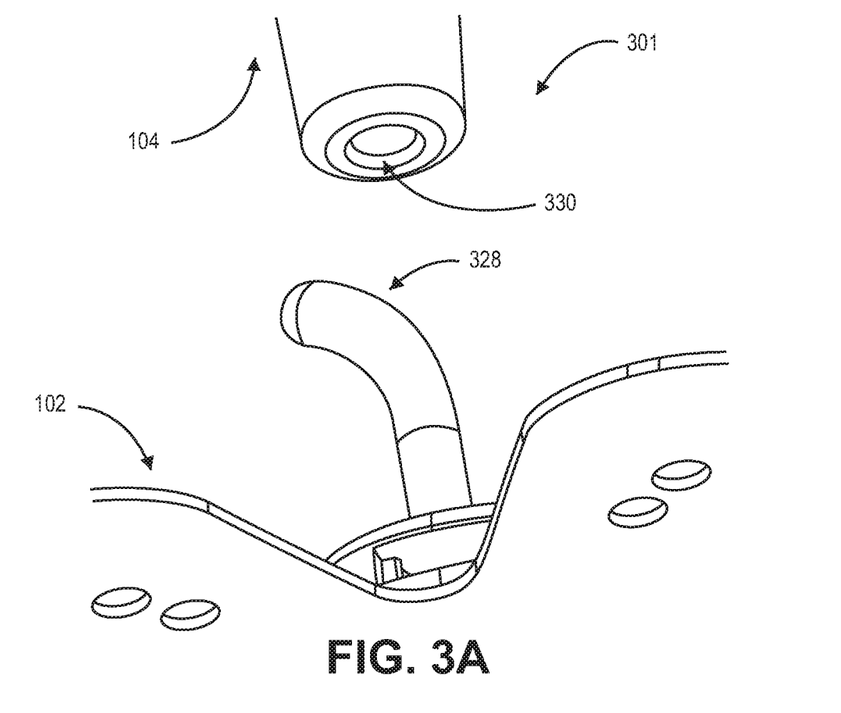
FIG. 3A is exploded view of a lock-block shield device with a malleable stem connection that couples a shield and base in accordance with implementations of the present disclosure.
Figure 3B:
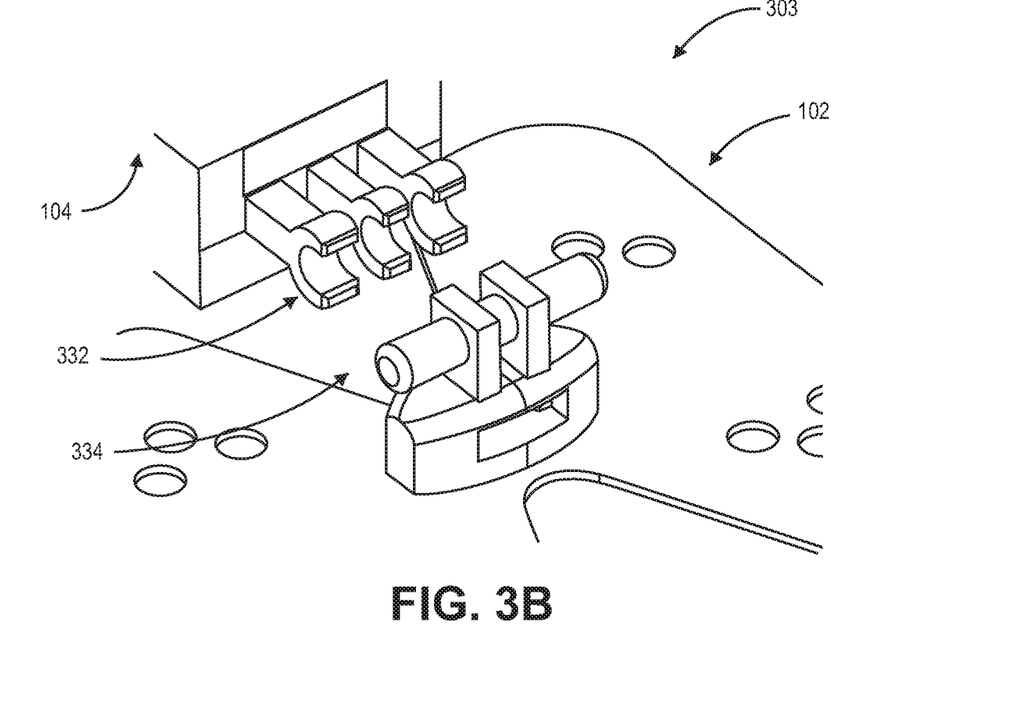

Referring to FIGS. 3, 3A, and 3B, other lock-block shield device features are now described. As noted above, these features can be used individually or in combination with the features illustrated and described with respect to FIGS. 1 and 2.

As illustrated in FIG. 3, the lock block 300 includes a ball and socket joint, respectively 322 and 324. The ball and socket joint can be used to couple the base 102 and shield 104 while permitting the shield/base to rotate and/or articulate with respect to the other component. Although the ball and/or socket can be formed from a variety of materials, in embodiments the ball is formed from a malleable metal or other malleable material that can be sized to fit in an aperture or recess formed in the base or locking mechanism. For example, the shield 104 is configured to rotate 360° about an axis that is generally perpendicular to the flap 106. The shield 104 can articulate with respect to the base 102 as well. For instance, the shield 104 can articulate along a second axis that is substantially perpendicular to that about which the rotation occurs. Accordingly, the shield 104 can tip forward and back along the second axis.

The ball and socket joint can include one or more stops to limit the extent to which the shield/base can articulate. Stops can be included to limit the shield from articulating more than plus or minus 30°. Although a lock-block shield device can include a clasp and a ball and socket joint, in embodiments a ball and socket can function as a clasp. For example, the socket 324 is configured to snap-fit with a ball shaped structure 322 on the opposite component (e.g., the base or the shield) to clasp the base 102 and shield 104 together. For example, a wire ball or wire socket can be used to connect with the clasp (e.g., door hinge structure or locking top with a hole for a wire to obtain a snug fit).

As illustrated in FIG. 3A, in an embodiment, a lock-block 301 includes a malleable stem 328 that couples the shield 104 to the base 102. The stem can be sufficiently malleable to allow it to at least partially deform when connected to the corresponding component. For example, the stem has a malleable end that fits in an aperture or recess 330 formed in one or more of the base, shield, or the locking mechanism. The stem 328 can be formed of a material that is sufficiently malleable to permit it to angle in multiple directions, such as to greater than 180 degrees in 2 planes and rotate 360 degrees with respect to the base or shield. In further embodiments, at least a portion of the stem 328 connects to a fixation slot formed adjacent to or in an aperture or recess in the base or base locking mechanism. Thus, for instance, an end portion of the stem is inserted in the slot and the door portion of a hinged clasp is closed at least partially about the end portion to secure it, e.g., hold it in a snug manner so the stem is capable of retaining a fixed position. Additionally, in embodiments implementing a wire base, the wire base can be configured to drop into the clasp as part of an attachment procedure.

As illustrated in FIG. 3B, the lock-block 303 includes a clasp that is configured to secure the base 102 and the shield 104 together. In embodiments, the clasp is a hinged clasp. For example, as can be seen in FIG. 3B the base 102 and the shield 104 are formed with corresponding structures (e.g., a "c" shaped clasp 332 that engages a cylindrical rod 334) that clasp the base and shield together. The clasp includes a securing mechanism in embodiments. Example securing mechanisms include a tab that is configured to engage a recess, a catch, or aperture on the opposing component, e.g., the base or the shield. The clasp can be configured to secure the shield and base without interfering with operation of the lock mechanism and/or operation of the shield.

Referring now to FIG. 3, construction and operation of a shield 104 in accordance with embodiments of the present disclosure are now described. The shield 104 can be formed of one or more layers of material that are designed to block the transmission of radiation through the shield 104. For example, the shield is composed of a sheet of a radiation blocking material, such as a lead foil 326, sandwiched between plastic layers. In embodiments, the shield offers radiation shielding equivalent to a lead layer.

Other suitable radiation blocking materials can be used as well including, but not limited to, tin or aluminum. In other embodiments, the plastic forming the shield can be infused with radiation blocking material, such as barium sulfate, a metal infused polymer (e.g., tantalum), that is mixed in the plastic. For example, the shield is formed of a plastic loaded with barium sulfate and/or tungsten. Barium sulfate may be selected because its weight is approximately two thirds or sixty-six percent (66%) that of lead. For example, a five by eight inch (5"×8") sheet of barium sulfate and/or tungsten loaded plastic can weigh approximately one quarter of a pound (0.25 lbs).

As shown, the shield 104 includes a lip 328 that extends about at least a portion of the shield's periphery. For instance, the shield 104 includes an extension or is curved, e.g., is concave, to prevent liquids such as blood and other bodily fluids from contacting a healthcare worker. For example, the lip 328 extends from a major surface of the shield. The shield 104 can be positioned so the lip 328 is directed to, for example, a physician to prevent blood from splashing on a physician's hands positioned on an opposite side of the shield 104.

The shield, in accordance with embodiments of the present disclosure, is adjustable to expand or contract to vary the extent to which the shield blocks radiation. For example, the shield 104 can be formed in multiple sections that fan out like a deck of playing cards or a paper fan. In this example, the shield 104 is composed of multiple sections that can slide or pivot past one another to expand or contract the area blocked by the shield.

In other embodiments, a shield 104 may include a central section from which one or more wing sections pivot or slide out of or into. Accordingly, a user can pivot or slide the wings to/from the central section to adjust the extent to which the shield extends, e.g., a half circle or a three quarter circle. It is to be apparent that the structures, techniques, and approaches described with respect to FIGS. 1-3B may be implemented in conjunction with the methods described below.

Example Methods

The following discussion describes methods that may be implemented in conjunction with a lock-block shield device described above. The methods are shown as a set of blocks that specify operations and are not necessarily limited to the order shown. In portions of the following discussion, reference may be made to the lock-block shield device 100 and/or its components. The techniques described below are independent of the structures described above, meaning that the techniques may be implemented in a variety of ways and are not necessarily limited to the structures illustrated in FIGS. 1-3.

Figure 4:
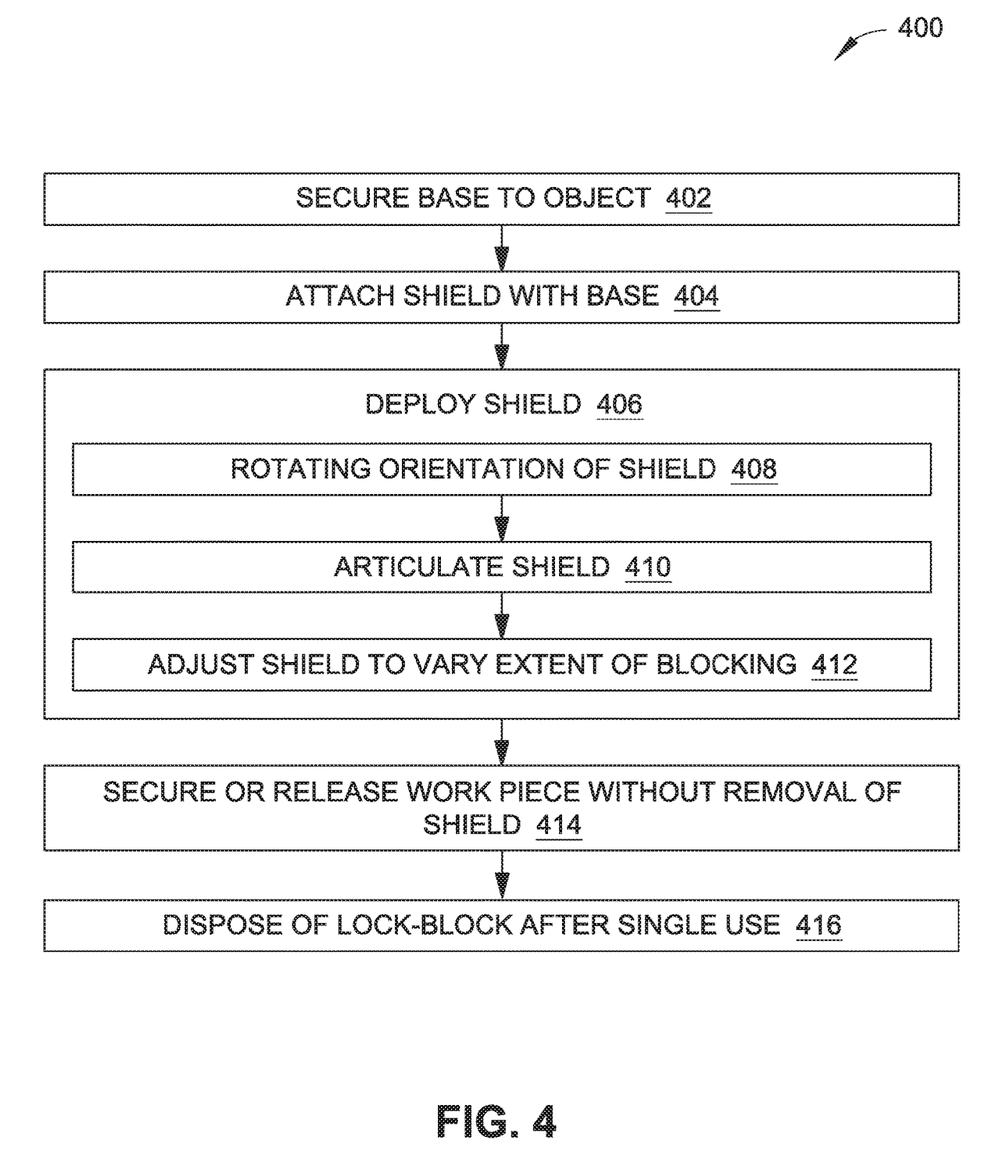
FIG. 4 is a flow diagram illustrating a method for reducing radiation exposure in a medical environment in accordance with example implementations of the present disclosure.

FIG. 4 depicts a method 400 in an example implementation for blocking radiation in a medical environment. The method may be used to block radiation from contacting a healthcare worker assisting a patient during a procedure in which the patient is exposed to at least some radiation.

As illustrated, a base is secured to an object (Block 402). The base may be secured to the object with an adhesive and/or a suture. The object in implementations is a patient or an object associated with a patient, such as a gown, a drape, or a table. For example, the base is sutured to the patient's gown to prevent it from coming loose.

A shield is attached with the base (Block 404). For example, the shield is snapped to the base using opposing structures included, respectively, on the base and shield. In embodiments, the shield attaches in a hinged manner and is secured in place by a friction tab that locks the opposing structures together. In other embodiments, a snap fit ball and socket joint is used to couple the base and shield together. For example, a ball may be press-fit into a socket formed by two or more fingers.

A shield is deployed (Block 406). The shield can be deployed depending on the situation to configure the shield to block radiation from contacting a healthcare worker treating a patient who is being exposed to at least some radiation. For example, the shield can be adjusted in a variety of ways based on the patient's position, the location of the radiation source, the healthcare worker's position, and so forth.

Optionally, a shield is rotated to orientate the shield (Block 408). For example, with the base secured, the shield is rotated to align the shield and prevent a physician's hands being exposed to radiation from an x-ray machine. The shield can be rotated 360° so the base can be placed in a manner that does not interfere with workflows and allow for ergonomic placement.

Optionally, a shield is articulated (Block 410). The shield can be articulated with respect to the base. For example, the shield 104 articulates +/−30° so it can be angled for a variety of factors. Example factors include, but are not limited to, the height and orientation of the patient, an x-ray source position, the position of the lock block shield device with respect to an area of interest, or a position of the physician or healthcare worker with respect to the lock-block shield device.

Optionally, the shield is adjusted to vary the extent to which the shield blocks radiation (Block 412). For example, the shield 104 can be adjusted to fan out in order to shield more area. Alternatively, the shield can be pivoted to contract the area that is shielded, e.g., by folding the shield's segments together. The shield, for instance, may extend approximately 180° when positioned on a table, but may fan-out to cover an angle of 225° when positioned on a patient's torso. In embodiments, segments forming the shield can pivot or slide past one another to expand to cover a greater portion or fold-up to decrease the shield's angular coverage orientation.

In embodiments, a lock mechanism is secured or released without removal of the shield (Block 414). For example, a lock mechanism 118 for securing a bile drain can be released without removing the shield 104 from the base 102 to which it is attached.

In embodiments, the shield is disposed of after a single use (Block 416). For example, the lock-block shield device including the shield is disposable to prevent pathogens from transferring between people such as patient and healthcare workers between uses. In additional embodiments, device or one of its components can be constructed so it can be sterilized for reuse.

Conclusion

Although the subject matter has been described in language specific to structural features and/or process operations, it is to be understood that the subject matter defined in the appended claims is not necessarily limited to the specific features or acts described above. Rather, the specific features and acts described above are disclosed as example forms of implementing the claims.

What is claimed is:

1. A medical radiation shielding device and fluid barrier, comprising:
   a substantially rigid shield having a lower edge, the shield configured to at least partially block radiation transmission through the shield; and
   a base configured to attach to the lower edge of the shield and at least partially block radiation transmission through the base, the base comprising a major surface, the base at least partially made from a polymer and a radiation-blocking material,
   wherein the shield is configured to attach to the base such that the shield extends in a direction away from the major surface of the base,
   wherein the shield is rotatable relative to the major surface of the base while attached to the base, and
   wherein the base is configured to attach to a patient such that the shield is supportable by the patient.

2. The medical radiation shielding device and fluid barrier of claim 1, wherein the shield is releasably attached with the base.

3. The medical radiation shielding device and fluid barrier of claim 1, wherein the shield is articulatable relative to the major surface of the base while attached to the base.

4. The medical radiation shielding device and fluid barrier of claim 1, wherein the shield and base are pivotally coupled by a ball and socket joint so that the shield is rotatable through 360° about an axis perpendicular to the major surface of the base.

5. The medical radiation shielding device and fluid barrier of claim 1, further comprising a malleable stem, the base and the shield coupled by the malleable stem such that the shield is positionable relative to the base by deformation of the malleable stem.

6. The medical radiation shielding device and fluid barrier of claim 1, wherein the radiation-blocking material of the base comprises barium.

7. The medical radiation shielding device and fluid barrier of claim 1, wherein the radiation-blocking material of the base is selected from the group consisting of barium, barium sulfate, tin, aluminum, and tantalum.

8. The medical radiation shielding device and fluid barrier of claim 1, wherein the shield is sterilizable for reuse, and the base is configured to be separable from the sterilizable shield.

9. A medical radiation shielding device and fluid barrier, comprising:
   a substantially rigid shield having a lower edge, the shield configured to at least partially block radiation transmission through the shield;
   a base configured to attach to the lower edge of the shield and at least partially block radiation transmission through the base, the base comprising a major surface, the base at least partially made from a polymer and a radiation-blocking material; and
   a malleable stem, the base and the shield coupled by the malleable stem such that the shield is positionable relative to the base by deformation of the malleable stem,
   wherein the shield is configured to attach to the base such that the shield extends in a direction away from the major surface of the base,
   wherein the malleable stem extends from the major surface of the base, and the shield comprises an aperture configured to receive the malleable stem, and
   wherein the base is configured to attach to a patient such that the shield is supportable by the patient.

10. A medical radiation shielding device and fluid barrier, comprising:
    a shield configured to at least partially block radiation transmission through the shield, the shield attachable to a base such that the shield extends in a direction away from the major surface of the base;
    the base comprising a malleable stem extending from a major surface of the base, the base configured to at least partially block radiation transmission through a major surface of the base, the base at least partially made from a polymer and a radiation-blocking material, and the malleable stem configured to releasably engage with a complementary mating feature of the shield such that the shield is articulatable relative to the major surface of the base while attached to the base,
    wherein the base is configured to attach to a patient such that the shield is supportable by the patient.

11. The medical radiation shielding device and fluid barrier of claim 10, wherein the complementary mating feature is an aperture is located along a lower edge of the shield and configured to receive the malleable stem.

12. The medical radiation shielding device and fluid barrier of claim 11, wherein the shield is sterilizable for reuse, and the base is configured to be separable from the sterilizable shield.

13. The medical radiation shielding device and fluid barrier of claim 12, wherein the shield is rotatable relative to the major surface of the base while attached to the base.

14. The medical radiation shielding device and fluid barrier of claim 12, wherein the radiation-blocking material of the base is selected from the group consisting of barium, barium sulfate, tin, aluminum, and tantalum.

15. The medical radiation shielding device and fluid barrier of claim 11, wherein the malleable stem is capable of retaining a fixed position.

* * * * *